United States Patent [19]
Funanage et al.

[11] Patent Number: 5,882,868
[45] Date of Patent: Mar. 16, 1999

[54] METHOD OF DIAGNOSING SPINAL MUSCULAR ATROPHY

[75] Inventors: Vicky Linn Funanage, Wilmington, Del.; Mena Scavina, Philadelphia, Pa.

[73] Assignee: The Nemours Foundation, Jacksonville, Fla.

[21] Appl. No.: 824,701

[22] Filed: Apr. 14, 1997

[51] Int. Cl.$^6$ .............................. C12Q 1/68; C07H 21/04; C12P 19/34
[52] U.S. Cl. .......................... 435/6; 435/91.2; 536/24.31; 536/24.33
[58] Field of Search ................... 435/6, 91.2; 536/24.31, 536/24.33; 935/8, 78

[56] References Cited
PUBLICATIONS

G. Van der Steege et al. PCR–based DNA test to confirm clinical diagnosis of autosomal recessive spinal muscular atrophy, The Lancet, vol. 345, pp. 985–986, Ap. 15, 1995.
E. Berry–Kravis et al. Polymerase Chain Reaction Assay for Detection of Spinal Muscular Atrophy Heterozygotes, Annals of Neurology, vol. 40, No. 2, p. 294, Aug., 1996
N. R. Rodrigues et al., Gene deletions in spinal muscular atrophy, J. Med. Genet., 1996, 33:93–96.
J–G Chang et al., Molecular Basis of Spinal Muscular Atrophy in Chinese, Am. J. Hum. Genet., 57:1503–1505, 1995.
N. Roy et al., The Gene for Neuronal Apoptosis Inhibitory Protein Is Partially Deleted in Individuals with Spinal Muscular Atrophy, Cell, vol. 80, pp. 167–178, Jan. 13, 1995.
S. Lefebvre et al., Identification and Characterization of a Spinal Muscular Atrophy–Determining Gene, Cell, vol. 80, pp. 155–165, Jan. 13, 1995.
F. Capon et al., Deletion Analysis of SMN and NAIP Genes in Spinal Muscular Atrophy Italian Families, Muscle & Nerve, 19:378–380 1996.
C. H. Wang et al., Characterization of survival motor neuron (SMN$^T$) gene deletions in asymptomatic carriers of spinal muscular atrophy, Human Molecular Genetics, 1996, vol. 5, No. 3, pp. 359–365.

E. Velasco et al., Molecular analysis of the SMN and NAIP genes in Spanish spinal muscular atrophy (SMA) families and correlation between number of copies of $^C$BCD541 and SMA phenotype Human Molecular Genetics, 1996, vol. 5, No. 2, pp. 257–263.

M. Scavina et al., A Multiplex PCR Technique to Screen for Deletions in Both the SMN and NAIP Genes 1997 AAN Scientific Program Abstract Submission, Feb. 20, 1997.

Four Spinal Muscular Atrophy articles on the Internet of Canadian neurologist dated Aug. 30, 1995 and others.

Schwartz, m. et al., Quantification, by solid–phase minisequencing, of the telomeric and centromeric copies of the survival motor neuron gene in families with spinal muscular atrophy, Human Molecular Genetics, 1997, vol. 6, No. 1, pp. 99–104.

Gomer et al, Cancer Research (1988) 48: 4 539–4 542.

*Primary Examiner*—Carla J. Myers
*Attorney, Agent, or Firm*—J. Michael Martinez de Andino; McGuire, Woods, Battle & Boothe LLP

[57] ABSTRACT

A diagnostic method for determining whether an individual is affected with spinal muscular atrophy involves evaluating the relative amounts of exon 5 of Neuronal Apoptosis Inhibitory Protein (NAIP) and exon 7 of centromeric and telomeric Survival Motor Neuron (SMN) genes in a genomic sample from the subject. A PCR analysis employing NAIP5F, NAIP5R, SMNX7DRA and SMNR111 primers is used to amplify the desired genes. The PCR product is digested with an enzyme which recognizes only the centromeric SMN sequence and the digested product can be separated by electrophoresis. The novel method allows multiplex analysis for both NAIP and SMN genes in the same sample work up. The analytical procedure further permits the digestion to be carried out without prior purification of the PCR product. Very importantly, the analytical procedure provides for the ability to diagnose the heterozygous telomeric SMN phenotype and thus allows the non-affected carrier of spinal muscular atrophy to be identified.

19 Claims, 4 Drawing Sheets

METHOD OF DIAGNOSING SPINAL MUSCULAR ATROPHY

FIELD OF THE INVENTION

This invention relates to an analytical procedure for diagnosing spinal muscular atrophy disorder in humans.

BACKGROUND AND SUMMARY OF THE INVENTION

Spinal muscular atrophy ("SMA") is the second most common neuromuscular disease in children after Duchenne muscular dystrophy. SMA refers to a debilitating neuromuscular disorder which primarily affects infants and young children. This disorder is caused by degeneration of the lower motor neurons, also known as the anterior horn cells of the spinal cord. Normal lower motor neurons stimulate muscles to contract. Neuronal degeneration reduces stimulation which causes muscle tissue to atrophy.

The atrophy from SMA is chiefly concentrated in the trunk and proximal muscles of the limbs. It can be more extensive and is typically accompanied by generalized weakness. Patients generally have difficulty clearing secretions, and consequently, severe respiratory complications are frequent. Other common complications include contractures and scoliosis. SMA adversely impacts upon a patient's quality of life and generally contributes to a reduced lifespan. Presently, there is no treatment or cure for SMA.

SMA is classified in different ways, however, three major categories are generally recognized. Type I, which is manifest from birth through about three months, is the most severe. Infants are born weak, have little spontaneous movement, lack head control and have problems feeding and breathing. Also called Werdnig-Hoffman disease, Type I typically results in death by the age of about three years.

Type II SMA is an intermediate form of the disorder which develops between about three and thirty-six months. Depending on the degree of weakness and respiratory involvement, life span can be very short, though longer than in Type I. In some cases, patients with Type II SMA can live into adulthood. SMA Type III or Kugelberg-Welander disease is characterized by weakness which usually becomes evident after the age of two years. The chief symptom is proximal muscle weakness. Type III victims usually live through adolescence to young adulthood. A rare, generally mild form of SMA disorder also is known to attack adults between the ages of 15 and 50.

SMA is now known as a genetically inherited condition. The most frequently observed inheritance pattern is autosomal recessive, however, autosomal dominant and X-linked forms are known as well. Recently, two genes on the long arm of chromosome 5 have been identified as markers for the disorder, namely, telomeric Survival Motor Neuron ($SMN^T$) and Neuronal Apoptosis Inhibitory Protein (NAIP). Aberrations of $SMN^T$ have been shown in SMA patients. (Lefebvre, S. et al. *Identification and Characterization of a Spinal Muscular Atrophy-Determining Gene*, Cell 80: 155–165, 1995.) Complete deletions or truncations of the $SMN^T$ gene were observed in 98.6% of SMA patients and the complementary population had either short deletions or point mutations of the gene. All controls tested positive for the presence of the $SMN^T$ gene. NAIP has also been found to be absent from some SMA patients as well as some asymptomatic relatives of SMA patients. (Roy, N., et al. *The Gene for Neuronal Apoptosis Inhibitory Protein is Partially Deleted in Individuals with Spinal Muscular Atrophy*, Cell 80: 167–178, 1995). The NAIP gene has several copies on chromosome 5. All of the copies are missing exon 5 and thus are non-functional.

The exact roles that $SMN^T$ and NAIP genes play in the mechanism which causes SMA is not yet fully understood. $SMN^T$ deletion or mutation correlates extremely well with the disorder. It also is suspected that NAIP deletion in combination with $SMN^T$ deletion can indicate more severe manifestations. Hence, it is usually very desirable to analyze for both $SMN^T$ and NAIP defects in diagnosis of SMA.

Formerly, tools for diagnosing SMA were limited to observing externally identifiable symptoms, muscle biopsy evaluation and electromyography. With the discovery of marker genes, genetic testing methods have developed. The genetic tests known in the art generally involve the steps of obtaining a sample of cells from the patient; extracting genomic DNA therefrom; amplifying the genomic DNA, for example, by polymerase chain reaction (PCR) technology using primers developed to reproduce marker gene sequences; and analyzing the PCR product to detect the absence or presence of the marker gene.

Conventional analytical methods involve carrying out separate analytical procedures for each of the two marker genes. DNA is amplified separately using primers specific for the respective genes. Independent electrophoretic gel separation procedures are conducted and results analyzed.

Such conventional methods are wasteful and inefficient. They consume larger amounts of sample and reagent materials and more human resources than might be necessary if the analyses could be performed simultaneously in a single laboratory work up. In addition, separate determinations are expensive in equipment cost and time. That is, separate sample work-ups might be run consecutively in one set of equipment, but the time to complete an analysis will be long. This delays diagnosis and incurs high labor costs. Analysis might be made shorter by running the separate analyses simultaneously on different pieces of equipment, however, this requires a greater investment in laboratory equipment. Prior to the present invention, simultaneous analysis for $SMN^T$ and NAIP genes using a single sample work-up was not possible. Primers suitable for simultaneous PCR amplification of both $SMN^T$ and NAIP were not known in the art.

A single analytical method to determine both $SNN^T$ and NAIP would reduce the cost and/or time to obtain a diagnosis for spinal muscular atrophy and is much desired. Accordingly, the present invention provides a set of nucleic acid primers for replicating the NAIP gene in polymerase chain reaction consisting of NAIP5F (SEQ ID No:1) and NAIP5R (SEQ ID NO:2). There is also provided a set of nucleic acid primers for replicating the $SMN^T$ gene consisting of SMNX7DRA (SEQ ID NO:3) and SMNR111 (SEQ ID NO:4). The two sets of primers can be employed in concert to amplify NAIP, $SMN^C$ and $SMN^T$ genes simultaneously in a single PCR procedure. $SMN^C$ is a centromerically located gene homologous to $SMN^T$. It is instrumental in performing the novel diagnostic method as will be explained in detail, below.

The present invention further provides an improved method of diagnosing spinal muscular atrophy disorders. The method involves analyzing for $SMN^T$ gene and NAIP gene abnormalities in a single sample of DNA from a subject individual. In one aspect, the invention is a method of diagnosing spinal muscular atrophy in a subject individual comprising the steps of:

(a) obtaining a sample of genomic DNA from the subject individual;

(b) performing polymerase chain reaction on the sample using primers selected to amplify selected exons of NAIP, $SMN^C$ and $SMN^T$ genes, wherein all the primers are present simultaneously in the polymerase chain reaction, thereby forming a Subject PCR Product having a NAIP DNA portion, an $SMN^C$ DNA portion and an $SMN^T$ DNA portion;

(c) digesting the Subject PCR Product with a restriction enzyme selected to cleave only the $SMN^C$ DNA portion present; thereby producing a cleaved $SMN^C$ DNA portion of the Subject PCR Product.

(d) determining relative amounts of the NAIP DNA, the cleaved $SMN^C$ DNA and the $SMN^T$ portions present in the Subject PCR Product; and (e) assigning to the subject individual a positive diagnosis of spinal muscular atrophy provided that a cleaved $SMN^C$ DNA portion is present in the Subject PCR Product and $SMN^T$ portion is absent from the Subject PCR Product.

Because no treatment or cure for SMA is currently available, it is especially desirable to identify individuals who are susceptible to the disease. As mentioned, spinal muscular atrophy is primarily an autosomal recessive trait. Consequently, a child will not develop SMA if only one of its parents has a gene mutation. Furthermore the child will only have a 25% risk of developing the disorder if both parents carry single copies of the mutated genes. The discovery of a genetic marker offers the possibility of a preventive therapy through genetic counseling, provided that heterozygous individuals can be identified.

Traditional analytical methods are not able to detect single copy deletions or truncations in the NAIP and $SMN^T$ genes. Consequently, no genetic method existed to identify SMA carriers. Current methods of determining the SMA gene mutation carrier status are based upon so-called linkage analysis. This technique involves recognizing an historical kindred relationship in which the subject disorder was evident. Linkage analyses are very difficult to conduct because evaluation of the health condition of individuals related to the patient over many generations is required. The necessary information for linkage analysis frequently is unavailable or of poor quality. As a result, the reliability of linkage analysis is very low. Hence, it is desirable to provide a simple, practical, and highly reliable method for identifying heterozygotes for SMA marker genes.

Accordingly, the present invention further provides a method of determining whether an individual is likely to be a carrier of the SMA disorder genotype, i.e., a person who possesses only one copy of the $SMN^T$ gene. Thus, in another aspect, the invention as set forth in the procedure outlined above further comprises after step (e) the step of assigning to the subject individual a diagnosis for significant probability of being heterozygous for the $SMN^T$ gene, provided that a cleaved $SMN^C$ DNA portion is present in the Subject PCR Product and that the relative amount of the $SMN^T$ portion is about equal to the relative amount of the $SMN^C$ portion.

In still another aspect, the present invention provides a diagnostic method for SMA which compares results obtained from analysis of a sMA-healthy sample to the test subject. This method comprises the steps of:

(a) obtaining a sample of genomic DNA from the subject individual;

(b) obtaining a control sample of genomic DNA from a sMA-healthy control individual;

(c) performing separate polymerase chain reactions upon each of the samples of genomic DNA using primers selected to amplify selected exons of NAIP, $SMN^C$ and $SMN^T$ genes, wherein all the primers are present simultaneously in each polymerase chain reaction, thereby forming a Subject PCR Product and a Control PCR Product, each PCR product having a NAIP DNA portion, a $SMN^C$ DNA portion and a $SMN^T$ DNA portion;

(d) separately digesting the Subject PCR Product and the Control PCR Product with a restriction enzyme selected to cleave only the $SMN^C$ DNA present; thereby producing Subject PCR Product and Control PCR Product each having a cleaved $SMN^C$ DNA portion;

(e) simultaneously determining the relative amounts of the NAIP DNA, the cleaved $SMN^C$ DNA and the $SMN^T$ portions in each of the Subject PCR Product and the Control PCR Product;

(f) assigning to the subject individual a positive diagnosis of spinal muscular atrophy provided that a cleaved $SMN^C$ DNA portion is present in the Subject PCR Product and that the $SMN^T$ portion is absent from the Subject PCR Product; and (g) determining the relative amounts of each of the cleaved $SMN^C$ DNA portion and the $SMN^T$ DNA portion in each of the Subject PCR Product and the Control PCR Product;

(h) assigning to the subject individual a diagnosis for high probability of being heterozygous for the $SMN^T$ gene provided that
  (i) a cleaved $SMN^C$ DNA portion is present in each of the Subject PCR Product and the Control PCR Product;
  (ii) in the Subject PCR Product, the relative amount of $SMN^T$ DNA portion is about equal to the relative amount of $SMN^C$ DNA portion; and
  (iii) the ratio of the relative amount of $SMN^T$ DNA portion in the Subject PCR Product to the relative amount of $SMN^C$ DNA portion in the Subject PCR Product is about half of the ratio of the relative amount of $SMN^T$ DNA portion in the Control PCR Product to the relative amount of $SMN^C$ DNA portion in the Control PCR Product.

DETAILED DESCRIPTION

Figure 1:
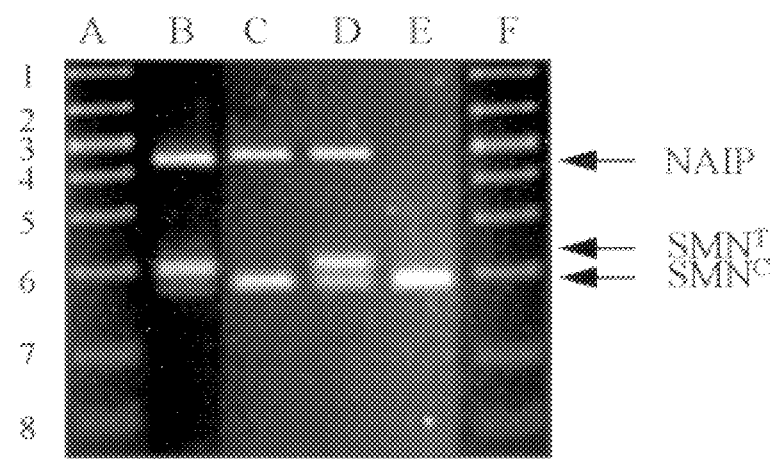
FIG. 1 is a scanned image of selected lanes of an electrophoresis gel showing typical results according to the novel diagnostic procedure of samples from SMA-healthy, SMA-affected and SMA carrier test subjects.

Deletions and truncations in both pairs of the survival motor neuron gene, $SMN^T$, located on the long arm of chromosome 5 were identified by Lefebvre et al. as determinative of spinal muscular atrophy disorder. $SMN^T$ is approximately 20,000 base pairs long and encodes a protein containing 294 amino acids. The exact function of this protein is not presently understood. An homologous gene, hereinafter called $SMN^C$, lies centromeric of $SMN^T$ on chromosome 5. $SMN^C$ is present in the overwhelming majority of the population, i.e., it is found in virtually all SMA patients and in about 95% of SMA-healthy individuals.

Certain parts of exon 7 of $SMN^T$ (SEQ ID NO:5) and of exon 7 of $SMN^C$ (SEQ ID NO:6) are both 188 base pairs. They are identical except for the single base pair at sequence position 164. The diagnostic method of this invention exploits the ability of restriction enzyme Dra I to recognize the six member nucleic acid sequence TTTAAA which is present at position 162–167 in $SMN^C$ (SEQ ID NO.:6) but not at all in $SMN^T$ (SEQ ID NO.:5). Dra I is able to selectively cut $SMN^C$ into two fragments which can be quantitatively differentiated from $SMN^T$ by appropriate methods. With respect to the survival motor neuron gene, the novel method involves digesting the polymerase chain reaction (PCR) product of genomic DNA with Dra I to cleave $SMN^C$ sequences to short fragments and long fragments of approximately 24 and 164 base pairs, respectively. When separated by electrophoresis, the short sequence fragments migrate completely through the gel. $SMN^C$ long sequence fragments and $SMN^T$ sequence fragments in the PCR product migrate at about the same rate and will appear as closely adjacent bands in stained electrophoresis gel.

The detection of both $SMN^C$ and $SMN^T$ fragments is an important feature of the method of diagnosing SMA. The appearance of a $SMN^C$ electrophoresis band helps to assure against false positive determinations. SMA is diagnosed by noting the absence of a $SMN^T$ electrophoresis band which is the consequence of deletion of the $SMN^T$ gene. If the diagnostic method analyzed for $SMN^T$ only, an empty lane on the electrophoresis gel would signify a positive diagnosis. However, the diagnostician could not know for certain whether the absence of a band was caused by the absence of the gene or an analytical procedure error. Because the $SMN^C$ gene is universally present in SMA patients with a $SMN^T$ deletion, a SMA-affected sample always produces an electrophoresis band. Analysis for both $SMN^T$ and $SMN^C$ genes should always result in the appearance of at least one band and thus would prevent false positive diagnoses by confirming that absence of a $SMN^T$ band corresponds to a true gene deletion.

Roy et al. have similarly shown that mutations of the functional copy of the neuronal apoptsis inhibitory gene, NAIP, can be a marker for certain SMA disease phenotypes. More specifically, deletion of NAIP exon 5, "NAIP5", (SEQ ID NO:7) may correlate with existence of SMA, and usually, with the more severe types. Exon 5 is one of the first two encoding exons of the functional NAIP gene which are deleted in approximately 67% of type I SMA chromosomes compared with 2% deletion in non-SMA chromosomes. Heretofore, deletions of NAIP5 have been detected by observing the absence of an electrophoresis band corresponding to NAIP5 in PCR product generated from genomic DNA. As explained above in connection with the analysis for detecting $SMN^T$ deletions, it is desirable to concurrently analyze for a control sequence to guard against false positive diagnoses. The exon 13 sequence (SEQ ID NO:8) which is universally present on the NAIP gene and its non-functional copies is available for this purpose. Accordingly, a conventional analytical method for diagnosing SMA based upon assay for NAIP usually includes procedures for PCR amplification and detection of both exon 5 and exon 13 NAIP gene sequences.

The analyses for $SMN^T$ and NAIP heretofore have only been conducted separately. In one aspect, the present invention provides for multiplex analysis for deletion of the $SMN^T$ and NAIP genes. The term "multiplex" means that the analytical method involves PCR amplification of all three of $SMN^C$ $SMN^T$ and NAIP genes, digestion of the $SMN^C$ gene, and electrophoresis separation steps together in a single sample work-up procedure. The multiplex analysis thus can detect a deletion of either or both $SMN^T$ and NAIP genes simultaneously. The novel analytical method notably incorporates determination of the $SMN^C$ gene PCR amplification product which provides a quality control check for false positive diagnoses. It also obviates the need to analyze for NAIP exon 13. Furthermore, the novel diagnostic procedure employs primers and a PCR temperature profile cycle that are compatible with the amplification of all sequences to be replicated. Hence, the present invention provides the beneficial feature of greatly simplifying the analytical methods formerly known in the art.

The novel diagnostic method involves obtaining genomic DNA from a test individual; using certain PCR primers to simultaneously amplify NAIP5, $SMN^C$ and $SMN^T$ sequences that may be present in a single sample; digesting the PCR product with a restriction enzyme to cut the $SMN^C$ gene; depositing the digested PCR products onto a gel; and separating the fractions, preferably with an electrophoresis gel procedure, to determine the relative amounts of the $SMN^C$, $SMN^T$ and NAIP5 components. The relative amounts of the subject sequences is determined by staining the gel and measuring the intensities of optically apparent bands. The relative amounts of gene sequences present in the PCR product are representative of the respective relative amounts in the genomic DNA. Finally, conclusions concerning the existence of SMA disorder in the test individual can be drawn by evaluating the relative amounts of the observed gene sequences according to various conditional criteria more fully explained, below.

The genomic DNA of the test individual can be obtained from any convenient source of nucleus-containing cells in the body. Mature red blood cells which do not possess a nucleus are perhaps the only human cells that cannot furnish genomic DNA. The sampling to obtain DNA should subject the tested individual to as little as possible risk of harm, discomfort, and anxiety. Therefore, non-invasive sampling techniques, such as sampling peripheral whole blood for lymphocytes and scraping buccal cells from inside the cheek, are preferred.

When whole blood is taken, 5 cm$^3$ is usually sufficient. Once taken, the blood sample should be sealed from the environment in a manner known in the medical arts for preserving the integrity of a biological material and to prevent disease transmission. The sample is preferably treated with an effective amount of an anticlotting agent, such as ethylene diamine tetraacetic acid (EDTA) or acid citrate dextrose (ACD). Heparin, a well known and widely used anticlotting agent, is not recommended for use in the present invention. Heparin can inhibit both PCR amplification and digestion of the isolated DNA. The amount of anticlotting agent above the minimum necessary to keep the sample fluid is not particularly critical. Most likely it will be desired to analyze the sample for SMA diagnosis directly, however, the sample can be stored at about 4° C. for up to about 3 days prior to analysis without detriment.

Isolation of genomic DNA from whole blood samples can be performed by known methods, such as lyzing the cell membrane with appropriate chemical agents, removing protein by high salt precipitation and concentrating the DNA by precipitation in isopropanol. Commercial DNA isolation tools are available for this purpose. An example is the Puregene DNA isolation kit from Gentra Systems, Inc., Minneapolis, Minn. Gentra Systems recommends dilution to attain 100 µg/ml, however it has been found that concentration of the isolated DNA to about 0.1 to about 1 mg/ml is also suitable. Concentration and purity can be confirmed by methods well known in the art, such as spectrophotometric absorbance. For example, the ratio of absorbance at 260 nm to absorbance at 280 nm, i.e., ($A_{260}/A_{280}$), should be in the range of about 1.6–2.0, and preferably, about 1.8.

Preferably, buccal cells should be lyzed immediately and preserved in lysis solution if not analyzed immediately. DNA then can be isolated as above by removing protein by high salt precipitation and by concentrating the DNA with isopropanol along with an inert carrier such as glycogen.

PCR forward primer SMNX7DRA (SEQ ID NO:3) and reverse primer SMNR111 (SEQ ID NO:4) can be used to replicate survival motor neuron gene exon 7 sequences $SMN^T$ (SEQ ID NO:5) and $SMN^C$ (SEQ ID NO:6). The primers have nucleic acid sequences in the 5'-3' direction, shown in the sequence listing, below. These primers can be made commercially and may be obtained from Cruachem Inc., Dulles, Va., for example. The same primers are described by van der Steege et al., The Lancet, 345: 985–986 (Apr. 15, 1995). Primers also can be made with a DNA synthesizer on site. Primers are usually provided lyophylized. They are reconstituted in sterile HPLC water to a final concentration of about 100 pmols/µL.

The forward primer NAIP5F (SEQ ID NO:1) and reverse primer NAIP5R (SEQ ID NO:2) can be synthesized by commercial contractors as above from the sequence information disclosed herein. The primers thus supplied are reconstituted in HPLC water to a final concentration of about 100 pmols/µL. These primers are used to replicate the neuronal apoptosis inhibitory protein gene exon 5 sequence (SEQ ID NO:7).

Equal molar amounts of NAIP5F and NAIP5R are combined and diluted with an equal volume of sterile water. Likewise, equal molar amounts of SMNX7DRA and SMNR111 are combined and diluted with an equal volume of sterile water. The NAIP5F/NAIP5R and SMNX7DRA/SMNR111 primer solutions are mixed together then used as a single reagent in the PCR replication process to perform a multiplex analysis of genomic DNA according to this invention. In the mixture, the amount of NAIP5F/NAIP5R preferably is approximately half the amount of SMNX7DRA and SMNR111. For example, for PCR amplification of about 500 nanograms of genomic DNA, 12.5 pmols of NAIP5F and 12.5 pmols of NAIP5R, are combined with 25 pmols of SMNX7DRA and 25 pmols of SMNR111. The volume then is adjusted to total 50 µL by further addition of sterile water.

PCR amplification generally is carried out with 500 ng of genomic DNA in 1× Taq buffer; 5% dimethyl sulfoxide; 150 µM dNTPs; mixed primer solutions, as described in the preceding paragraph; and 1.25 units of Taq polymerase. Taq buffer consists of 16.7 mM Tns-HCl, pH 8.8; 170 µg/ml bovine serum albumin; 16.7 mM ammonium sulfate; 6.7 mM magnesium chloride; 6.8 mM EDTA and 10 mM β-mercaptoethanol. The temperature profile consists of an initial 6 minute period at 94° C.; 30 cycles of a two minute sequence composed of 30 s at 94° C., 30 s at 50° C. and 1 minute at 65° C. A final extension step of 6 minutes at 65° C. follows.

Next, the PCR product is digested with a restriction enzyme selective for the $SMN^C$ sequence. Dra I is a preferred enzyme for this purpose. Dra I is available from New England Biolabs, Beverly, Mass. in 50% glycerol solution with 50 mM KCl, 10 mM Tris-HCl (pH 7.4), 0.1 mM EDTA, 1 mM dithiothreitol, and 200 µg per ml bovine serum albumin. Preferably 0.5 µL of this Dra I solution is diluted with 9.5 µL sterile water and added to 10 µL of the PCR amplification product. Reaction is completed by holding the mass quiescent at about 37° C. for about 0.5–1.5 hours. Following digestion, the product should contain amplified amounts of nucleotide fragments corresponding to NAIP5, $SMN^C$, and $SMN^T$ in proportion to the respective amounts of the source sequences in the genomic DNA.

In addition to providing advantages such as combining two sample work-ups into one, the present invention possesses the beneficial feature that the PCR product need not be purified prior to the digestion step. Surplus reagents, stray contaminants and reaction by-products normally are present in PCR nucleotide amplification product. These materials frequently inhibit reaction of an enzyme in subsequent digestion steps. Conventionally, PCR product is purified to remove the undesirable contaminants prior to digestion. The purification adds to the time and cost of the analysis. It also wastes some of the PCR product that becomes entrained in the contaminants discarded in the purification steps. The digestion system of the present invention can successfully operate in the presence of unpurified PCR product. Accordingly, the need for the added purification steps with attendant PCR product yield loss is eliminated.

In the next steps of the diagnostic procedure, the NAIP5, $SMN^T$ and $SMN^C$ fragments present in the digested PCR product are separated and the relative amounts of each fragment type are quantified. Known electrophoresis and gel staining methods can be employed. In a preferred procedure, 10 µL of the digestion product is placed on a 3–4% vol/vol agarose separation gel, such as 3 vol NuSieve/1 vol SeaKem agarose gel from FMC Corp., Rockland, Ma. The product can be electrophoretically stimulated to migrate through the gel. Preferred conditions are 100 V applied for about 60–90 minutes. A suitable dye can be used to stain the resulting separated bands. The gel can be photographed or scanned to record appearance and to perform numerical analysis of the band intensities. Thereafter the scanned image and band intensities can be loaded into a electronic digital computer running appropriate software to analyze the relative band intensities from the scanned images.

The Eagle Eye Still Video imaging system from Stratagene, La Jolla, Calif., is representative of a commercial product for recording the band intensities of ethidium bromide-stained gel samples. Gelreader software from National Center for Supercomputing Applications ("NCSA") is representative of computer software designed to analyze the band intensity data generated from the imaging system. Ethidium bromide is a commonly used dye for staining. Gel is stained in a solution of 10 ng/ml ethidium bromide in water. SYBR® Green I or SYBR® Green II nucleic acid gel stains are dyes gaining popularity in this field and which can be used in the present invention. These dyes generally are more sensitive than ethidium bromide and are capable of producing more clearly defined bands. However, gels stained with SYBR Green I and II stains require the use of specially adapted imaging systems, such as the Fluorescence Scanning System of Molecular Dynamics, Co. The chief function of the computer and software is to automate the steps of identifying the bands produced by each sample; recording the raw intensity differential relative to background of each band; and optionally, to perform calculations using the intensity data. For example, the imaging, scanning and computing system can measure intensity at different distances across the width of a band and thus can provide an accurate average intensity for each band. The functions can be performed manually just as well, if not as quickly or accurately, using densitometry to measure band intensity. A standard molecular weight marker is used to indicate band size. Presently available versions of Gelreader software require placing standard molecular weight marker in the first and last lanes of the electrophoresis gel. Representative of standard markers suitable for use with the present invention are the low molecular weight intensity markers from Fisher Scientific Co., Pittsburgh, Pa. Future versions of Gelreader software or different band intensity data software may have different requirements.

The average band intensity is an indicator of the relative quantity of fragments which are present in the PCR product. It is understood in the art that the relative fragment quantities in the PCR product are proportional to the relative amounts of counterpart DNA sequence in the genomic sample.

FIG. 1 is a scanned image of selected lanes of an electrophoresis gel containing bands generated by analyzing samples obtained from different individuals according to the diagnostic procedure of the present invention. Bands 1–8 in lanes A and F correspond to different DNA base pair fragments in standard compositions of increasing molecular weight. The standards are used both visually and by software to benchmark the positions of experimental bands shown in lanes B–E.

Lane B represents the band intensity spectrum produced by control DNA from a person who is healthy for SMA in all respects. That is, both copies of the person's chromosome 5 contain $SMN^T$ and the functional copy of NAIP also is present. The bands corresponding to NAIP5, $SMN^T$ and $SMN^C$ are labeled appropriately in the figure. Normally, the multiplex analysis according to the present invention produces the NAIP5 band above and apart from the $SMN^T$ and $SMN^C$ bands. The latter bands are usually quite close to each other due to the similarity of the base pair lengths. The $SMN^T$ band will appear above the $SMN^C$ band.

All three bands are present in lane B. The presence of a moderately intense NAIP5 band signifies the existence of NAIP gene in the genome. As shown in FIG. 1, the $SMN^T$ band of a SMA-healthy individual usually will appear more intense than the $SMN^C$ band.

Lane C shows a band spectrum of a SMA-affected patient. Of the two SMN bands, only $SMN^C$ is present. Absence of the $SMN^T$ band signifies deletion of the $SMN^T$ gene that is a hallmark of SMA. The fact that each of the NAIP5 and $SMN^C$ bands appears validates that the deletion of $SMN^T$ is real. It is possible that an incorrectly performed analysis could cause the $SMN^T$ band not to show up. Because the multiplex method analyzes for $SMN^C$ which is always present in SMA-affected patients, a $SMN^C$ must appear when the patient has a $SMN^T$ deletion. Lane E illustrates the situation which demonstrates the great value of analyzing for the $SMN^C$ band. It shows the band intensity spectrum of a SMA patient whose NAIP5 band is absent. The absence of the NAIP5 band may correlate with enhanced severity of SMA. That is, NAIP5 deletions are found mostly in Type I SMA patients and seldom in Type III SMA patients. Again, the existence of the $SMN^C$ band in its proper location verifies that the absence of the other two bands probably was not caused by error in performing this particular analytical determination.

The band spectra illustrated-in lanes B, C and E demonstrate how the present method can be used to diagnose spinal muscular atrophy in a patient. The novel method also provides the ability to diagnose whether an individual is a carrier for the disease. That is, the diagnostic procedure can detect the likelihood that a test subject is heterozygous for the $SMN^T$ gene. Lane D of FIG. 1 shows an electrophoresis band spectrum obtained by the novel analytical method for an individual who is at high risk of being an obligate carrier of SMA. Surprisingly a good correlation was identified between SMA carriers and the electrophoresis spectrum in which intensities of the $SMN^T$ and $SMN^C$ gene electrophoresis bands are about equal.

Figure 2:
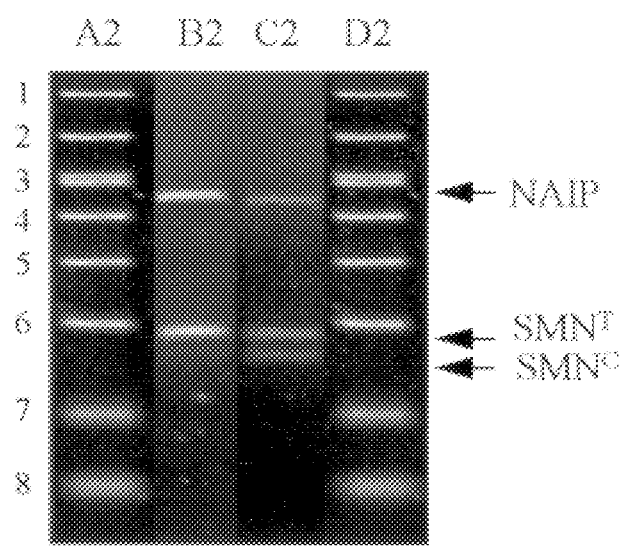
FIG. 2 is a scanned image of selected lanes of an electrophoresis gel showing typical results according to the novel diagnostic procedure of samples from a SMA-healthy control subject and a SMA carrier test subject.

The determination that the $SMN^T$ and $SMN^C$ band intensities are about equal can be made subjectively by visual observation or objectively by numerical analysis. This aspect of the invention can best be understood with reference to FIG. 2. Lanes B2 and C2, show electrophoresis bands resulting from analysis according to the present invention of samples from a SMA-healthy person (a "Control" subject) and an obligate carrier, respectively. Electrophoresis bands of a molecular weight standard are shown in lanes A2 and D2. The $SMN^T$ and $SMN^C$ bands in lane C2 visually appear about equally intense. By comparison, the Control $SMN^T$ band is very much brighter than the Control $SMN^C$ band. The numerical values for intensity of the B2 and C2 lane bands determined by image scanning analysis and calculation with Gelreader software are presented in Table 1.

With regard to numerical analysis of electrophoresis band intensities, the term "about equal intensity" has a slightly unconventional meaning. It means that a $SMN^T/SMN^C$ band intensity ratio is in the range of about 1–2. From Table 1 it is seen that the band intensity ratio of the carrier's sample is $2,250/1,226=1.84$.

Often the diagnosis for risk of being a SMA carrier can be based solely on finding about equal intensity of the $SMN^T$ and $SMN^C$ bands of the subject individual without regard to the band intensity of a Control sample. However, reliability of the diagnosis for risk of being a SMA carrier can be improved using a Control. More particularly, the ratio of the $SMN^T$ to $SMN^C$ intensities of the test subject has been discovered to be approximately half the corresponding ratio observed in a concurrently analyzed Control. Hence, it has been discovered that persons at high risk for carrying a single copy of a $SMN^T$ gene defect, and thus who are capable of passing the genetic mutation associated with SMA to their offspring, can be identified by evaluating electrophoresis band intensities against these criteria.

Table 1 reveals how an objective criterion for determining SMA carrier status is established by comparing the test subject's band intensity results to those of a Control. The $SMN^T/SMN^C$ band intensity ratio of lane C2 is about half that of the corresponding ratio of the Control bands in Lane C2. That is, the carrier $SMN^T/SMN^C$ band ratio of 1.84 divided by the Control ratio (i.e., 3.73) is 0.49.

TABLE 1

|  | B2 Control | C2 SMA Carrier |
|---|---|---|
| NAIP5, intensity units | 2362 | 3703 |
| $SMN^T$, intensity units | 1677 | 2250 |
| $SMN^C$, intensity units | 449 | 1226 |
| $SMN^T/SMN^C$, ratio | 3.73 | 1.84 |
| C2 Ratio / B2 Ratio |  | 0.49 |

In most cases, the $SMN^T/SMN^C$ band intensity ratio of a high risk SMA carrier will be about 0.25–0.75 times the $SMN^T/SMN^C$ ratio of a SMA-healthy Control measured concurrently. By "measured concurrently" is meant that the PCR amplification and digestion steps for both the test subject and control samples are carried out about the same time and using reagents from the same stock batches, the same equipment, e.g., PCR machine, and the same operating conditions. Preferably, the amplification and digestion steps for the Control will be performed within a seven day period, and more preferably, within a one day period of the test subject. Additionally, the amplification/digestion products should be separated for quantification on the same electrophoresis gel. Theoretically, there should be no significance attached to performing the subject and control analyses far apart in time from each other. However, in a practical sense, it is desirable to carry out analyses of the subject and the control at conditions as closely alike as possible to reduce the probability of introducing significant variability into the procedure. If a $SMN^T/SMN^C$ ratio less than about 0.25 is observed, the diagnostician should consider whether incomplete digestion is the cause, in which case, re-analysis would be indicated.

Numerical values of band intensities also can be used to provide more objective test criteria for determining a $SMN^T$ deletion leading to a positive diagnosis of SMA. As previously stated, to make such a determination, the $SMN^C$ band should be evident in the electrophoresis band spectrum. One can infer the presence of the $SMN^C$ band if the intensity of the $SMN^C$ band of the subject PCR product is at least one percent of the $SMN^C$ band intensity of the control PCR product. Furthermore, to establish a positive diagnosis for SMA, the $SMN^T$ band or both NAIP5 and $SMN^T$ bands should be absent. In numerical terms, absence of NAIP5 or $SMN^T$ DNA can be established by observing that the intensity of the gene band of the subject PCR product is less than one percent of the intensity of the corresponding gene band of the control PCR product.

The genomic DNA for the control can be obtained from any person known to be SMA-healthy. Validation that the person donating the control genomic DNA is SMA-healthy can be made by traditional diagnostic methods such as by linkage analysis, by clinical observation for absence of SMA signs and symptoms, by electromyography, by muscle biopsy, by analysis according to the present invention or by a combination of these methods. The Control subject preferably should be a mature adult having a family history free of SMA. An analysis by the present method of a SMA-healthy subject will reveal an electrophoresis band spectrum containing all three bands and the ratio of $SMN^T/SMN^C$ band intensities will be unequal. The Control DNA can also be obtained from a standard artificially maintained cell line cultivated from an individual who is SMA-healthy. By "artificially maintained" is meant that the cell line is preserved by a facility suitably equipped to provide for long term, multiple sampling of genomic DNA from an original source of cell. Use of a standard cell line as the source of Control DNA provides a basis for comparing diagnostic results according to this invention which may be determined at different laboratories. It also obviates the need to ascertain whether the control DNA selected for use in a particular diagnostic determination is SMA-healthy. For example, the standard cell line of sample accession No. CRL1509 available from American Type Culture Collection ("ATCC"), Manassas, Va. can be used as the Control for this diagnostic method.

This invention is now illustrated by examples of certain representative embodiments thereof, wherein all parts, proportions and percentages are by weight unless otherwise indicated. All units of weight and measure not originally obtained in SI units have been converted to SI units.

EXAMPLES

In the examples, the following multiplex analytical procedures were used to generate electrophoresis bands from DNA obtained from peripheral blood samples of Control and test subjects.

Procedure A: Isolation of DNA from peripheral blood samples

About 3–5 mL of venous blood from an individual was placed in each of two EDTA-coated 5 mL evacuated blood sample containers. Each blood sample was transferred to a 15 mL centrifuge tube containing 9 mL of RBC lysis agent as supplied in the Gentra Puregene™ DNA Isolation Kit, catalog No. D-5000, Gentra Systems, Inc., Minneapolis, Minn. Blood and lysis agent were mixed by inverting each tube 1–2 times. The tubes were then held at room temperature for fifteen minutes.

The lysis product was centrifuged for 10 minutes at 2500×g and the supernatant liquid was decanted and discarded. The pellets were resuspended by vortexing and 1 mL of Gentra Systems cell lysis solution was added to each tube and mixed by pipetting. The tubes were stored for 14–18 hours at room temperature. Fifteen µL RNase was added to each tube and mixed by inversion 25 times. The sample tubes then were held in a 37° C. water bath for about 15–60 min.

To each tube was added 1 mL of Gentra Systems "protein precipitation solution" which was mixed by vortexing for 20–30 s. The tubes were centrifuged for 10 minutes at 2500×g and the supernate was collected into 15 mL tubes which each contained 3 mL isopropanol. The isopropanol was mixed with the sample by tube inversion 50 times. Precipitated DNA from each tube was removed with a plastic rod to separate 1.5 mL Eppendorf tubes containing 1 mL of 70% 200 proof ethanol in sterilized, high pressure liquid chromatography-grade water. The Eppendorf tubes were centrifuged for 3–5 minutes at 15000×g. Supernatant liquid was discarded and the pellets were air-dried. The pellets were resuspended in about 100–200 µL Gentra Systems DNA hydration solution. The suspended genomic DNA from both Eppendorf tubes was then combined in a single Eppendorf tube and mixed by gently flicking the tube.

Procedure B: Amplification and Digestion of DNA

Ten µL of the genomic DNA was combined with 990 µL DEPC-treated water. Each diluted sample was transferred to a quartz cuvette for quantitative analysis by spectrophotometric absorbance, A, at 260 and 280 nm using a Pharmacia Genequant-II RNA/DNA calculator. The concentration of DNA in the sample was calculated using GeneQuant's calibration formula of 1 optical density absorbance units per 50 mg/ml DNA. The genomic DNA was diluted with DEPC-treated water to obtain a manageable concentration of about 100 ng DNA/µL.

Five hundred ng of genomic DNA was dispensed into a 0.5 cm³, thin-walled PCR tube. To the PCR tube was further added 45 µL of PCR mix which consisted of: 10 µL 5×Taq buffer; 2.5 µL dimethyl sulfoxide; 12.5 pmols NAIP5F primer; 12.5 pmols NAIP5R primer; 25 pmols SMNX7DRA primer; 25 pmols SMNRIII primer, 27.25 µL sterile water; dNTPs; and 0.25 µL Taq polymerase source. The PCR mix and DNA were mixed by pipetting; then 50 µL mineral oil was added. The sample was placed in a Perkin Elmer model 480 PCR machine which was run for one initial cycle of 6 minutes at 94° C.; 30 two-minute cycles of 30 s at 94° C., 30 s at 50° C. and 1 minute at 65° C.; and one final extension cycle of 6 minutes at 65° C.

Ten µL of PCR product was placed into a 500 µL Eppendorf tube, to which was added 9.5 µL sterile water, and 0.5 µL Dra I restriction enzyme. The tube was shaken gently and spun for about 1–3 seconds to drain material clinging on the walls to the bottom of the tube. The tube was then placed in a 37° C. water bath for 30 minutes to digest $SMN^C$ nucleic acid sequences.

Procedure C: Separation and quantification of PCR products.

Five μL dye was added to the digestion product and mixed by pipetting. At least 10 μL of the digestion product was placed into a well of a 4% Nusieve (FMC Corporation) agarose gel between standard molecular weight markers in end lane positions and separated by electrophoresis under 100 V for 1 hour. The standard molecular weight markers had base pair lengths of 1000, 700, 525, 500, 400, 300, 200, 100 and 50. Due to the proximity of the bands produced by the 525 and 500 base pair standards, the two bands are identified collectively by the reference numeral "3" in the figures. The gel was stained by immersion in an ethidium bromide solution for 15 minutes. An image of the resulting bands in the gel were obtained using an Eagle Eye still video imaging system from Stratagene Co. The image was transferred to an Apple Macintosh Quadra 800 computer on which relative band intensities were analyzed using NCSA Gelreader version 2.07 software.

Examples 1–8

Figure 3:
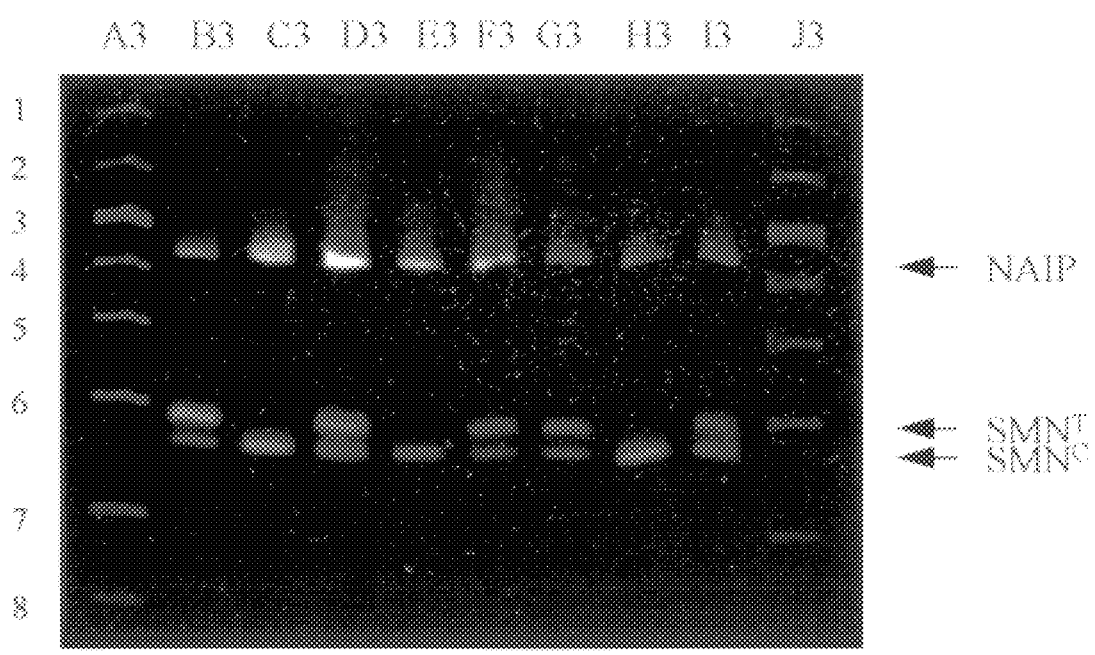
FIG. 3 is a scanned image of an electrophoresis gel showing band spectra according to the present invention of samples obtained from a Control subject, and SMA-healthy, SMA-affected and SMA carrier test subjects.

Peripheral blood samples were obtained from 8 test subjects who have been diagnosed positively for SMA, identified as obligate carriers of SMA gene mutations, or known to be SMA-healthy. The samples were worked up according to Procedure A to extract genomic DNA. The DNA samples were concurrently amplified and digested according to Procedure B. Finally the fragments in the PCR product were separated and quantified by electrophoresis as described in Procedure C on a single sheet of gel. The resulting electrophoresis bands are shown in FIG. 3. Computer software-generated electrophoresis band intensities and the SMA status of each sample are presented in Table 2. The ratios of $SMN^T/SMN^C$ band intensities for each sample, and the sample band intensity ratio divided by the control band intensity ratio of Example 1 were calculated and also recorded in the table.

Lane B3 contains the results of digested PCR product of a 24 year old adult female, who did not show symptoms of SMA and who did not have a family history of SMA. The band spectrum in lane B3 exhibits all the signs of a Control. As in each test lane of FIG. 3, a very intense NAIP5 band is seen alongside the molecular weight standard bands 3–4. Additionally, in B3 both $SMN^T$ and $SMN^C$ bands also appear and the $SMN^T$ band is substantially brighter than the $SMN^C$ band. Numerical band intensities reveal that the $SMN^T/SMN^C$ ratio is 2.5 which is significantly greater than 2.0 and thus, not about equal. The data derived from Ex. 1 was thus used as the Control for analyzing the results of Examples 2–8.

Blood samples from individuals known to have SMA were used to create the $SMN^T$ band spectra shown in lanes C3, E3 and H3. Each of these results reveals the complete absence of the $SMN^T$ band. This type of band spectra signifies deletion of the $SMN^T$ gene deletion from the genomic DNA of the test subjects. Accordingly, the $SMN^T/SMN^C$ ratios for these samples numerically calculate to zero. The novel method thus can be used to accord a positive diagnosis for SMA.

The samples used to generate the results shown of lanes D3, F3, G3 and I3 were obtained from individuals who were identified as obligate carriers of SMA. The test subjects were adults who were asymptomatic for SMA themselves, but whose offspring had the disease. Each of the band spectra from Examples 3, 5, 6 and 8 contain a $SMN^T$ band that appears about equally intense as the $SMN^C$ band. The numerical $SMN^T/SMN^C$ band intensity ratios of these examples are all within the range of 1–2. As mentioned above, a second indication of SMA carrier status is that the ratio of $SMN^T$ to $SMN^C$ band intensities of the carrier is about half of the corresponding band ratio of the Control. This second tell-tale characteristic is observed from the spectra of FIG. 3 by dividing the $SMN^T/SMN^C$ band intensity ratios of Ex. 3, 5, 6 and 8 by 2.50 which is the corresponding ratio of the Control subject determined in Ex. 1. The numerical results range from 0.42 to 0.68. These examples show that the novel method can be used to diagnose an individual as being SMA-healthy, SMA positive or an asymptomatic carrier for SMA.

TABLE 2

| Ex. | Lane | NAIP5 | $SMN^T$ | $SMN^C$ | Sample $SMN^T/SMN^C$ | Sample $SMN^T/SMN^C$ Control $SMN^T/SMN^C$ | SMA Status |
|---|---|---|---|---|---|---|---|
| | | Band Intensity | | | | | |
| 1 | B3 | 3777 | 2206 | 875 | 2.5 | 1.00 | Control: SMA Healthy |
| 2 | C3 | 5669 | 0 | 2120 | 0.00 | 0.00 | SMA Positive |
| 3 | D3 | 6169 | 2059 | 1200 | 1.70 | 0.68 | Highly probable SMA carrie ($SMN^T$ heterozygous) |
| 4 | E3 | 4515 | 0 | 1334 | 0.00 | 0.00 | SMA Positive |
| 5 | F3 | 4593 | 1207 | 732 | 1.65 | 0.66 | Highly probable SMA carrie |
| 6 | G3 | 3499 | 1336 | 834 | 1.60 | 0.64 | Highly probable SMA carrie |
| 7 | H3 | 3136 | 0 | 2054 | 0.00 | 0.00 | SMA Positive |
| 8 | I3 | 3722 | 1203 | 1126 | 1.06 | 0.42 | Highly probable SMA carrie |

Examples 9

A sample of accession No. CRL1509 human DNA was obtained from ATCC. Five μL of ATCC Accession No. CRL1509 DNA was amplified and ten μL of PCR Product was digested according to Procedure B. The NAIP5, $SMN^C$ and $SMN^T$ in the PCR product were separated and identified as described in Procedure C. The electrophoresis gel was obtained which exhibited bands corresponding to the PCR products of the three gene fragments. The $SMN^C$ band was more than equally intense as the $SMN^T$ band. The appearance of the electrophoresis gel spectrum validated that the donor of ATCC accession No. CRL1509 did not have $SMN^T$ gene deletion characteristic of SMA, and further, that the donor was not a heterozygous carrier of SMA.

Examples 10–17

Figure 4:
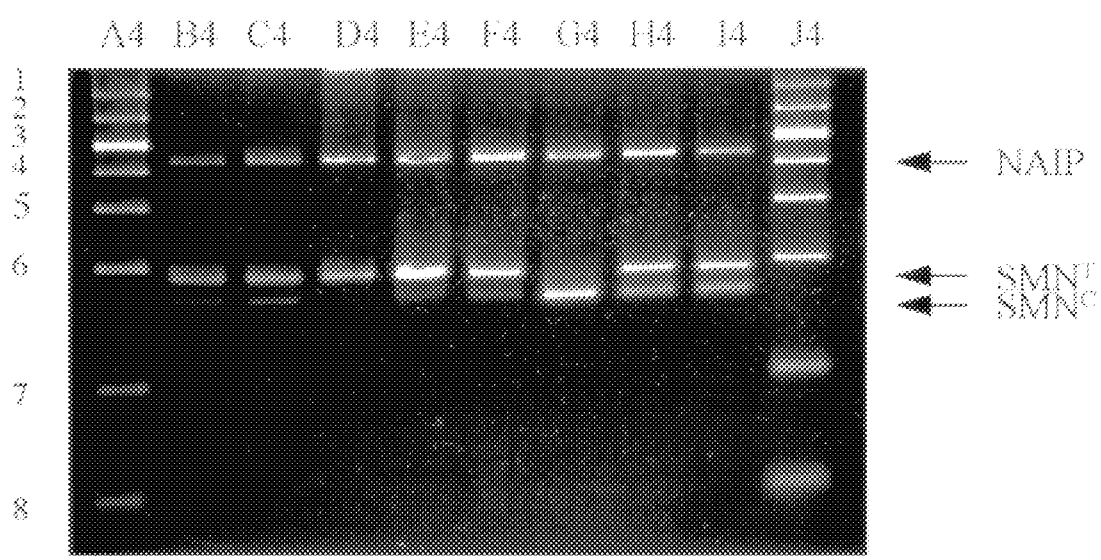
FIG. 4 is a scanned image of an electrophoresis gel showing band spectra according to the present invention of samples obtained from a preserved sample of human DNA and SMA-healthy, SMA-affected and SMA carrier test subjects.

DNA was obtained from these samples as described in Procedure A. For Example 10, 10 μL of human DNA from ATCC Control sample ATCC accession No. CRL1509 was obtained as in Example 9. For Examples 11–17, peripheral blood samples were obtained from seven test subjects who were diagnosed by techniques independent of the novel diagnostic method to have SMA, or to be obligate carriers of SMA gene mutations. The seven test subject DNA and Control DNA samples were concurrently amplified by PCR and digested with restriction enzyme as described in Procedure B. The PCR products were separated by electrophoresis as in Procedure C on the same sheet of gel. The resulting electrophoresis band spectra are shown in FIG. 4. The SMA-healthy Control sample is in lane B4. Computer software-generated electrophoresis band intensities and the SMA status of each sample are presented in Table 3. The ratios of $SMN^T/SMN^C$ band intensities for each sample, and the sample band intensity ratios divided by the Control band intensity ratio of Example 10 were calculated and also recorded in the table.

An NAIP gene band was found in each of Ex. 10–17. $SMN^T$ and $SMN^C$ bands were also present in the Control and the intensity ratio of these bands in the Control was 2.4. The numerical results are thus consistent with the conclusion drawn from visual appearance of the bands that the intensities are not about equal. Hence the according to the present invention the Control sample is diagnosed correctly as SMA healthy.

Electrophoresis band spectra for Examples 11–14 of SMA healthy subjects are in lanes C4 and F4, respectively. Visual inspection of FIG. 4 and observation that the numerical ratios are greater than about 2 indicate that the $SMN^T/SMN^C$ band intensity ratios are not about equal. Additionally, the band intensity ratios of these samples are substantially greater than half of the Control sample band intensity ratio. FIG. 4 shows that Examples 12 and 13 exhibit virtually no band for the centromeric SMN gene. Gelreader software of image analysis shows that the samples contain an extremely small amount of $SMN^C$ gene. These test subjects are from among the approximately 5% of SMA healthy individuals, mentioned above, who have an essential deletion of $SMN^C$ gene from their genomic DNA.

Example 15 shows the results obtained from a subject diagnosed with SMA. The $SMN^T$ band is absent entirely. This indicates a deletion of the $SMN^T$ gene. Examples 16 and 17 were taken from obligate carriers for SMA. Intensities of the $SMN^T$ and $SMN^C$ bands appear visually about equal in FIG. 4. The intensity ratios are 1.6 and 1.5 respectively. These are in the range of about 1 to 2 which is considered about equal. Also the intensity ratio of the test subject bands is within the range of about 0.25–0.75 of the corresponding ratio of the Control subject bands, i.e., about half the Control band intensity ratio.

Thus, the results shown in FIG. 4 and Table 3 show that the novel diagnostic method using results obtained from a SMA healthy Control subject can reliably discern between health conditions of SMA healthy, SMA affected and SMA carrier individuals.

TABLE 3

| Ex. | Lane | NAIP5 | $SMN^T$ | $SMN^C$ | Sample $SMN^T/SMN^C$ | Sample $SMN^T/SMN^C$ Control | SMA Status |
|---|---|---|---|---|---|---|---|
| | | Band Intensity | | | | | |
| 10 | B4 | 1491 | 2557 | 1069 | 2.4 | 1.00 | Control: SMA Healthy |
| 11 | C4 | 2408 | 2533 | 1204 | 2.1 | 0.88 | SMA Healthy |
| 12 | D4 | 2780 | 3626 | 438 | 8.3 | 3.46 | SMA Healthy |
| 13 | E4 | 3197 | 5102 | 606 | 8.4 | 3.5 | SMA Healthy |
| 14 | F4 | 3954 | 3964 | 1344 | 2.9 | 1.2 | SMA Healthy |
| 15 | G4 | 2991 | 0 | 3282 | 0.0 | 0.0 | SMA Positive |
| 16 | H4 | 2957 | 3832 | 2429 | 1.6 | 0.67 | Highly probable SMA carrier |
| 17 | I4 | 2804 | 3875 | 2612 | 1.5 | 0.63 | Highly probable SMA carrier |

What is claimed is:

1. A method of diagnosing a subject individual comprising the steps of:
   (a) obtaining a sample of genomic DNA from the subject individual;
   (b) performing polymerase chain reaction on the sample using primers selected to amplify selected exons of $SMN^C$ and $SMN^T$ genes, and primers selected to amplify selected exons of NAIP comprising exon 5 wherein all the primers are present simultaneously in the polymerase chain reaction, thereby forming a subject PCR product having a NAIP DNA portion, a $SMN^C$ DNA portion and a $SMN^T$ DNA portion;
   (c) digesting the subject PCR product with a restriction enzyme selected to cleave only the $SMN^C$ DNA portion present; thereby producing a cleaved $SMN^C$ DNA portion of the subject PCR product;
   (d) determining relative amounts of the NAIP DNA, the cleaved $SMN^C$ DNA and the $SMN^T$ portions present in the subject PCR product;
   (e) determining whether (1) a cleaved $SMN^C$ DNA portion is present in the subject PCR product and (2) $SMN^T$ portion is absent from the subject PCR product; and
   (f) identifying the subject individual as having spinal muscular atrophy when both (1) a cleaved $SMN^C$ DNA portion is present in the subject PCR product and (2) said $SMN^T$ portion is absent from the subject PCR product.

2. The method of claim 1 wherein the primers include NAIP5F (SEQ ID NO:1), NAIP5R (SEQ ID NO:2), SMNX7DRA (SEQ ID NO:3) and SMNR111 (SEQ ID NO:4).

3. The method of claim 2 wherein the selected exon of NAIP is exon 5, the selected exon of $SMN^C$ is exon 7 and the selected exon of $SMN^T$ is exon 7.

4. The method of claim 1 wherein the restriction enzyme is Dra I.

5. The method of claim 4 wherein the subject PCR product is not purified prior to the digesting step.

6. The method of claim 1 wherein the determining step includes separating the cleaved SMNC DNA portion, the NAIP DNA portion and the SMNT DNA portion by electrophoresis to produce bands of intensity proportional to the amounts of each of NAIP DNA, cleaved $SMN^C$ DNA and $SMN^T$ DNA portions present in the subject PCR product.

7. The method of claim 6 further comprising after step (f) the step of:
   (g) determining (1) the intensity of the band corresponding to the $SMN^T$ portion and (2) the intensity of the band corresponding to the $SMN^C$ portion;
   (h) determining whether the intensity of the band corresponding to the $SMN^T$ portion is about equal to the intensity of the band corresponding to the $SMN^C$ portion; and
   (i) identifying the subject individual as heterozygous for the $SMN^T$ gene when both (1) a cleaved $SMN^C$ DNA portion is present in the subject PCR product and (2) said $SMN^T$ portion is absent from the subject PCR product.

8. A method of diagnosing a subject individual comprising the steps of:
   (a) obtaining a sample of genomic DNA from the subject individual;
   (b) obtaining a control sample of genomic DNA from a SMA-healthy control individual;
   (c) performing separate polymerase chain reactions upon each of the samples of genomic DNA using primers selected to amplify selected exons of NAIP, $SMN^C$ and $SMN^T$ genes, wherein all the primers are present simultaneously in each polymerase chain reaction, thereby forming a subject PCR product and a control PCR product, each PCR product having a NAIP DNA portion, a $SMN^C$ DNA portion and a $SMN^T$ DNA portion;
   (d) separately digesting the subject PCR product and the control PCR product with a restriction enzyme selected to cleave only the $SMN^C$ DNA present; thereby producing subject PCR product and control PCR product each having a cleaved $SMN^C$ DNA portion;
   (e) simultaneously determining the relative amounts of the NAIP DNA, the cleaved $SMN^C$ DNA and the $SMN^T$ portions in each of the subject PCR product and the control PCR product;
   (f) determining whether (1) a cleaved $SMN^C$ DNA portion is present in the subject PCR product and (2) $SMN^T$ DNA portion is absent from the subject PCR product;
   (g) identifying the subject individual as having spinal muscular atrophy when both (1) a cleaved $SMN^C$ DNA portion is present in the subject PCR product and (2) said $SMN^T$ DNA portion is absent from the subject PCR product;
   (h) determining whether
      (1) a cleaved $SMN^C$ DNA portion is present in each of the subject PCR product and the control PCR product;
      (2) in the subject PCR product, the relative amount of $SMN^T$ DNA portion is about equal to the relative amount of $SMN^C$ DNA portion; and
      (3) the ratio of the relative amount of $SMN^T$ DNA portion in the subject PCR product to the relative amount of $SMN^C$ DNA portion in the subject PCR product is about half of the ratio of the relative amount of $SMN^T$ DNA portion in the control PCR product to the relative amount of $SMN^C$ DNA portion in the control PCR product; and
   (i) identifying the subject individual as heterozygous for the $SMN^T$ gene when (1) a cleaved $SMN^C$ DNA portion is present in each of the subject PCR product and the control PCR product; (2) in the subject PCR product, the relative amount of $SMN^T$ DNA portion is about equal to the relative amount of $SMN^C$ DNA portion; and (3) the ratio of the relative amount of $SMN^T$ DNA portion in the subject PCR product to the relative amount of $SMN^C$ DNA portion in the subject PCR product is about half of the ratio of the relative amount of $SMN^T$ DNA portion in the control PCR product to the relative amount of $SMN^C$ DNA portion in the control PCR Product.

9. The method of claim 8 wherein in place of determination steps (h)(2) and (h)(3), step (h) includes determining whether
- (4) the ratio of the relative amount of $SMN^T$ DNA portion to the relative amount of $SMN^C$ DNA portion in the subject PCR product is at most about 2; and
- (5) the ratio of the relative amount of $SMN^T$ DNA portion in the subject PCR product to the relative amount of $SMN^C$ DNA portion in the subject PCR product is about 0.25–0.75 of the ratio of the relative amount of $SMN^T$ DNA portion in the control PCR product to the relative amount of $SMN^C$ DNA portion in the control PCR product; and in step (i) the subject individual is identified as heterozygous for the $SMN^T$ gene when (1) a cleaved $SMN^C$ DNA Portion is present in each of the subject PCR product and the control PCR product, (4) the ratio of the relative amount of $SMN^T$ DNA portion to the relative amount of $SMN^C$ DNA portion in the subject PCR product is at most about 2; and (5) the ratio of the relative amount of $SMN^T$ DNA portion in the subject PCR product to the relative amount of $SMN^C$ DNA portion in the subject PCR product is about 0.25–0.75 of the ratio of the relative amount of $SMN^T$ DNA portion in the control PCR product to the relative amount of $SMN^C$ DNA Portion in the control PCR product.

10. The method of claim 9 wherein the primers include NAIP5F (SEQ ID NO:1), NAIP5R (SEQ ID NO:2), SMNX7DRA (SEQ ID NO:3) and SMNR111 (SEQ ID NO:4).

11. The method of claim 9 wherein the restriction enzyme is Dra I.

12. The method of claim 11 wherein the subject PCR product is not purified prior to the digesting step.

13. The method of claim 9 wherein the determining step (e) includes separating the cleaved $SMN^C$ DNA portion, the NAIP DNA portion and the $SMN^T$ DNA portion by electrophoresis to produce bands of intensity proportional to the amounts of each of NAIP DNA, cleaved $SMN^C$ DNA and $SMN^T$ DNA present in the subject PCR product and the control PCR product.

14. The method of claim 13 further comprising the step of
(j) determining whether
- (1) the ratio of the intensity of the $SMN^T$ band to the intensity of the $SMN^C$ band of the subject PCR product is at most about 2; and
- (2) the ratio of the intensity of the $SMN^T$ band of the subject PCR product to the intensity of the $SMN^C$ band of the subject PCR product is about 0.25–0.75 of the ratio of the intensity of the $SMN^T$ band of the control PCR product to the intensity of the $SMN^C$ band of the control PCR product; and (k) the subject individual is identified as heterozygous for the $SMN^T$ gene when both (1) the ratio of the intensity of the $SMN^T$ band to the intensity of the $SMN^C$ band of the subject PCR Product is at most about 2; and (2) the ratio of the intensity of the $SMN^T$ band of the subject PCR product to the intensity of the $SMN^C$ band of the subject PCR product is about 0.25–0.75 of the ratio of the intensity of the $SMN^T$ band of the control PCR product to the intensity of the $SMN^C$ band of the control PCR.

15. The method of claim 13 further comprising the step of
(j) determining whether
- (1) the intensity of the $SMN^C$ band of the subject PCR product is at least about one percent of the intensity of the $SMN^C$ band of the control PCR product, and
- (2) the intensity of the $SMN^T$ band of the subject PCR product is less than about one percent of the intensity of the $SMN^T$ band of the control PCR product; and (k) the subject individual is identified as having spinal muscular atrophy when both (1) the intensity of the $SMN^C$ band of the subject PCR product is at least about one percent of the intensity of the $SMN^C$ band of the control PCR product, and (2) the intensity of the $SMN^T$ band of the subject PCR product is less than about one percent of the intensity of the $SMN^T$ band of the control PCR product.

16. The method of claim 8 wherein the control sample of genomic DNA is obtained from a human cell line maintained in vitro.

17. The method of claim 16 wherein the control sample of genomic DNA is obtained from sample Accesion No. CRL1509 from the American Type Culture Collection.

18. The method of claim 1 wherein the primers consist of NAIP5F (SEQ ID NO:1), NAIP5R (SEQ ID NO:2), SMNX7DRA (SEQ ID NO:3) and SMNR111 (SEQ ID NO:4).

19. The method of claim 8 wherein the primers consist of NAIP5F (SEQ ID NO:1), NAIP5R (SEQ ID NO:2), SMNX7DRA (SEQ ID NO:3) and SMNR111 (SEQ ID NO:4).

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i i ) HYPOTHETICAL: no ( x i ) SEQUENCE DESCRIPTION: SEQ ID NO:1:

AAAGCCTCTG ACGAGAGGAT CTCC        24

( 2 ) INFORMATION FOR SEQ ID NO: 2:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (iii) HYPOTHETICAL:no (xi) SEQUENCE DESCRIPTION: SEQ ID NO: 2:

CCTCTCAGCC TGCTCTTCAG ATTC 24

(2) INFORMATION FOR SEQ ID NO: 3:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (iii) HYPOTHETICAL:no (xi) SEQUENCE DESCRIPTION: SEQ ID NO: 3:

CCTTCCTTCT TTTTGATTTT GTTT 24

(2) INFORMATION FOR SEQ ID NO: 4:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (iii) HYPOTHETICAL: no (xi) SEQUENCE DESCRIPTION: SEQ ID NO: 4:

AGACTATCAA CTTAATTTCT GATC 24

(2) INFORMATION FOR SEQ ID NO: 5:

(i) SEQUENCE CHARACTERISTICS:
    (A) LENGTH: 188 base pairs
    (B) TYPE: nucleic acid
    (C) STRANDEDNESS: double
    (D) TOPOLOGY: linear (ii) MOLECULE TYPE: Genomic DNA (iii) HYPOTHETICAL:no (x) PUBLICATION INFORMATION:
    (A) AUTHORS:Lefebvre, S. et al.
    (B) TITLE:Identification and Characterization of a Spinal
        Muscular Atrophy- Determining Gene
    (C) JOURNAL: Cell
    (D) VOLUME: 80
    (F) PAGES: 155-165
    (G) DATE: 1995

(xi) SEQUENCE DESCRIPTION: SEQ ID NO: 5:

AGACTATCAA CTTAATTTCT GATCATATTT TGTTGAATAA AATAAGTAAA ATGTCTTGTG 60

AAACAAAATG CTTTTTAACA TCCATATAAA GCTATCTATA TATAGCTATC TATGTCTATA 120

TAGCTATTTT TTTTAACTTC CTTTTATTTT CCTTACAGGG TTTCAAACAA AATCAAAAAG 180

AAGGAAGG 188

(2) INFORMATION FOR SEQ ID NO: 6:

(i) SEQUENCE CHARACTERISTICS:
    (A) LENGTH: 188 base pairs (B) TYPE: nucleic acid
(C) STRANDEDNESS: double
(D) TOPOLOGY: linear (ii) MOLECULE TYPE: Genomic DNA (iii) HYPOTHETICAL: no (xi) SEQUENCE DESCRIPTION: SEQ ID NO:6:

| AGACTATCAA | CTTAATTTCT | GATCATATTT | TGTTGAATAA | AATAAGTAAA | ATGTCTTGTG | 60 |
| AAACAAAATG | CTTTTTAACA | TCCATATAAA | GCTATCTATA | TATAGCTATC | TATGTCTATA | 120 |
| TAGCTATTTT | TTTTAACTTC | CTTTTATTTT | CCTTACAGGG | TTTTAAACAA | AATCAAAAAG | 180 |
| AAGGAAGG | | | | | | 188 |

(2) INFORMATION FOR SEQ ID NO: 7:

(i) SEQUENCE CHARACTERISTICS:
(A) LENGTH: 436 base pairs
(B) TYPE: nucleic acid
(C) STRANDEDNESS: double
(D) TOPOLOGY: linear (ii) MOLECULE TYPE: Genomic DNA (iii) HYPOTHETICAL: no (x) PUBLICATION INFORMATION:
(A) AUTHORS: Roy, N., et al.
(B) TITLE: The Gene for Neuronal Apoptosis Inhibitory Protein is Partially Deleted in Individuals with Spinal Muscular Atrophy
(C) JOURNAL: Cell
(D) VOLUME: 80
(F) PAGES: 167-178
(G) DATE: 1995

(xi) SEQUENCE DESCRIPTION: SEQ ID NO: 7:

| AAAGCCTCTG | ACGAGAGGAT | CTCCCAGTTT | GATCACAATT | TGCTGCCAGA | GCTGTCTGCT | 60 |
| CTTCTGGGCC | TAGATGCAGT | TCAGTTGGCA | AAGGAACTAG | AAGAAGAGGA | GCAGAAGGAG | 120 |
| CGAGCAAAAA | TGCAGAAAGG | CTACAACTCT | CAAATGCGCA | GTGAAGCAAA | AAGGTTAAAG | 180 |
| ACTTTTGTGA | CTTATGAGCC | GTACAGCTCA | TGGATACCAC | AGGAGATGGC | GGCCGCTGGG | 240 |
| TTTTACTTCA | CTGGGGTAAA | ATCTGGGATT | CAGTGCTTCT | GCTGTAGCCT | AATCCTCTTT | 300 |
| GGTGCCGGCC | TCACGAGACT | CCCCATAGAA | GACCACAAGA | GGTTTCATCC | AGATTGTGGG | 360 |
| TTCCTTTTGA | ACAAGGATGT | TGGTAACATT | GCCAAGTACG | ACATAAGGGT | GAAGAATCTG | 420 |
| AAGAGCAGGC | TGAGAG | | | | | 436 |

(2) INFORMATION FOR SEQ ID NO: 8:

(i) SEQUENCE CHARACTERISTICS:
(A) LENGTH: 250 base pairs
(B) TYPE: nucleic acid
(C) STRANDEDNESS: double
(D) TOPOLOGY: linear (ii) MOLECULE TYPE: Genomic DNA (iii) HYPOTHETICAL: no (xi) SEQUENCE DESCRIPTION: SEQ ID NO: 8:

| TGACCAGCTC | CTAGAGAAAG | AAGGATCTGT | TACTGAAATG | TGCATGAGGA | ACATTATCCA | 60 |
| GCAGTTAAAG | AATCAGGTCT | TATTCCTTTT | AGATGACTAC | AAAGAAATAT | GTTCAATCCC | 120 |
| TCAAGTCATA | GGAAAACTGA | TTCAAAAAAA | CCACTTATCC | CGGACCTGCC | TATTGATTGC | 180 |

```
TGTCCGTACA  AACAGGGCCA  GGGACATCCG  CCGATACCTA  GAGACCATTC  TAGAGATCCA      240

AGCATTTCCC                                                                  250
```